Oct. 10, 1950 J. A. BLASER Plant Pat. 982
DRACAENA PLANT
Filed Oct. 18, 1949
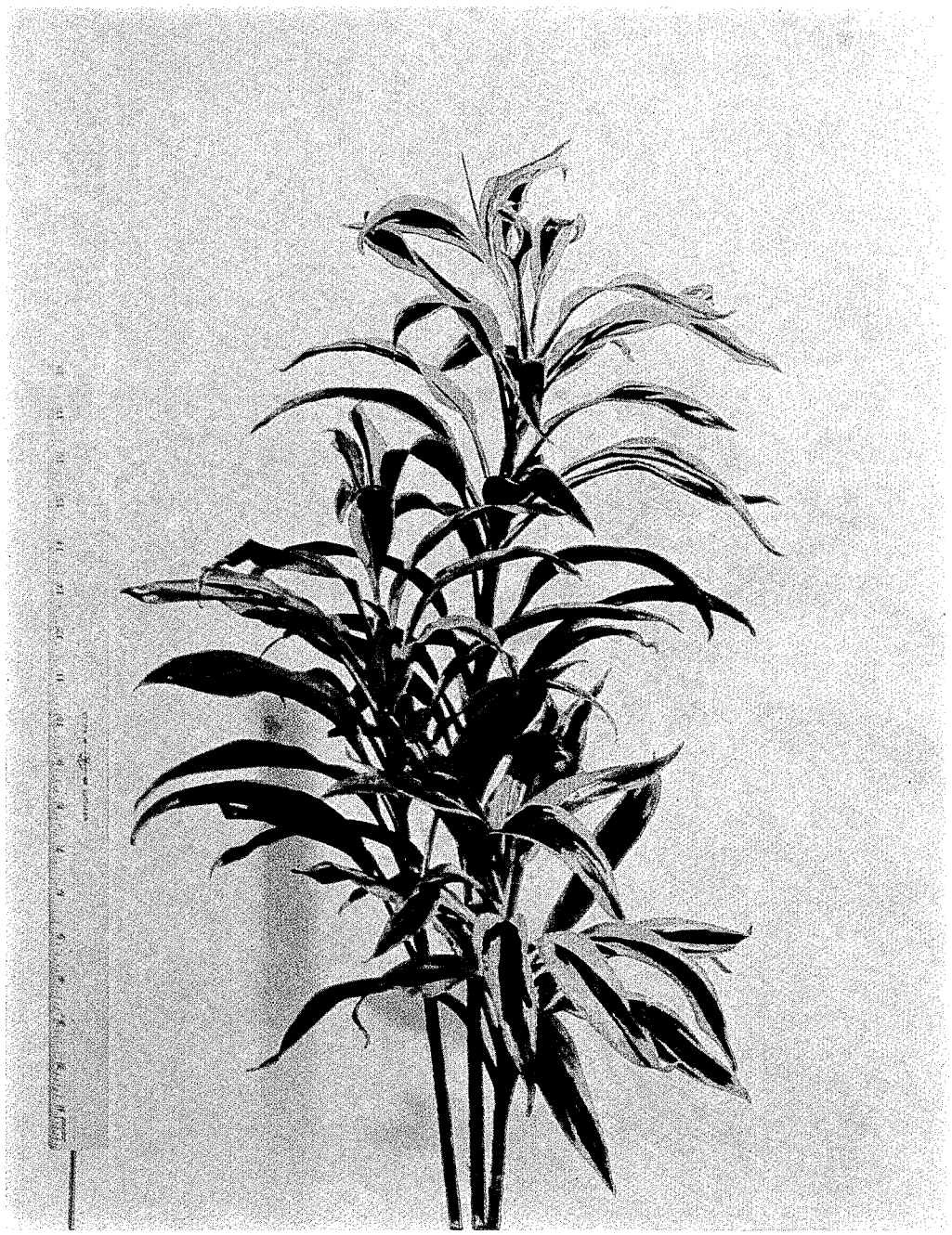
INVENTOR
John A. Blaser
By Orville M. Kile
PLANT PATENT AGENT Patented Oct. 10, 1950

Plant Pat. 982

UNITED STATES PATENT OFFICE

982

DRACAENA PLANT

John A. Blaser, Tallavast, Fla.

Application October 18, 1949, Serial No. 121,950

1 Claim. (Cl. 47—60)

My present discovery relates to a new and distinct variety of ornamental herbaceous plant known botanically as Dracaena and originating from the Cordyline family of such plants. It originated at my greenhouses in Tallavast, Florida, through definite efforts to obtain Dracaena varieties of more brilliant colors. A number of years ago we obtained a quantity of *Dracaena terminalis* and among them were many varieties of unknown origin but known to the trade by various names such as Lord Wallsey, Tri-Color, etc. Various ones of these varieties were crossed many times in trying to obtain more brilliant colors, and a few years ago the present variety was found as a sport on one of the unnamed plants of the Cordyline family obtained from these crosses.

This new variety has been asexually reproduced from cuttings, at our greenhouses in Tallavast, Florida, and its distinguishing characteristics have proved to be permanent.

The accompanying illustrations show an entire plant of this new variety of Dracaena in approximately its true colors. Alongside the plant is an 18-inch rule to show the relative height of the plant.

In the following description of my new variety, color plate numbers refer to Ridgway's Color Standards and Nomenclature. In other color references, the usual dictionary meaning is intended.

My new variety is distinctly different from all known varieties of Dracaena, particularly with respect to its more brilliant leaf coloring in which the green ranges from Spinach Green (Plate V) on the new top leaves, to Dark Dull Yellow Green (Plate XXXII) on the older leaves.

The purplish red coloring ranges from Spinel Red (Plate XXVI), Rosolane Purple and Tyrian Rose (Plate XII) to a bright crimson. Although the red and green appear in varying proportions, the green forms the center and the red the edge of the leaf. The under side of the leaf is approximately the same in color as the upper surface.

The plant is herbaceous and has small, narrow leaves, in contrast to the usual large, broad leaf of the Cordylines. In the early stages of its growth, the leaves of graduated size are closely grouped, forming a compact plant. Later the internodes lengthen and the plant becomes much taller (approximately one foot at the end of the first year and nearly two at the end of the second year). A portion of the base of the stalk is without leaves in the older plants, the leafless stalk lengthening each year by the dropping of the older leaves.

Petioles of the leaves are very short, particularly on the younger plants, and they spring from the nodes of the stem which are very close together. Leaves are irregularly variegated, having varying amounts of the two colors. Their texture is heavy and substantial.

This new variety propagates true from cuttings and roots with great ease from each eye or node when placed in earth. It makes an excellent decorative pot plant because of its dwarf size and brilliant foliage.

The known variety most like my new variety is *Dracaena sanderiana*, although the latter is not of the Cordyline family. My variety resembles Sanderiana in growth, size and shape, but has leaf coloring of green and brilliant red instead of the green and white of Sanderiana. In addition, my new variety propagates with greater ease under the same or similar conditions.

Having thus disclosed my discovery, I claim:

The new distinct variety of dracaena plant of the Cordyline family, substantially as herein shown and described, characterized particularly by its dwarf, compact growth; ease of propagation; and small narrow leaves with variegations of green and brilliant coloring ranging from purple to red.

JOHN A. BLASER.

No references cited.